United States Patent
DuBois (10) Patent No.: US 8,562,627 B2
(45) Date of Patent: Oct. 22, 2013

(54) DEVICE AND METHOD FOR HARVESTING AND IMPLANTING FOLLICULAR UNITS

(75) Inventor: Brian DuBois, Redwood City, CA (US)

(73) Assignee: Restoration Robotics, Inc, San Jose, CA (US)

(*) Notice: Subject to any disclaimer, the term of this patent is extended or adjusted under 35 U.S.C. 154(b) by 0 days.

(21) Appl. No.: 13/238,630

(22) Filed: Sep. 21, 2011

(65) Prior Publication Data
US 2012/0010631 A1 Jan. 12, 2012

Related U.S. Application Data

(63) Continuation of application No. 12/049,170, filed on Mar. 14, 2008, now Pat. No. 8,066,717.

(60) Provisional application No. 60/895,530, filed on Mar. 19, 2007.

(51) Int. Cl.
A61B 17/50 (2006.01)

(52) U.S. Cl.
USPC .............................................. 606/133

(58) Field of Classification Search
USPC .......... 600/566, 567, 184, 562–565; 606/130, 606/131, 133, 134, 184, 185, 187, 167, 170
See application file for complete search history.

(56) References Cited

U.S. PATENT DOCUMENTS

| | | | |
|---|---|---|---|
| 1,433,340 A | 10/1922 | Clark | |
| 3,515,128 A | 6/1970 | McEvoy | |
| 3,848,579 A * | 11/1974 | Villa-Real | 600/577 |
| 3,998,230 A | 12/1976 | Miller | |
| 4,160,453 A | 7/1979 | Miller | |
| 5,090,745 A | 2/1992 | Kluger | |
| 5,562,613 A | 10/1996 | Kaldany | |
| 5,584,841 A | 12/1996 | Rassman | |
| 5,591,186 A | 1/1997 | Wurster et al. | |
| 5,693,064 A | 12/1997 | Arnold | |
| 5,782,843 A | 7/1998 | Aasberg | |
| 5,782,851 A | 7/1998 | Rassman | |
| 5,782,853 A | 7/1998 | Zeevi et al. | |
| 5,792,163 A | 8/1998 | Hitzig | |
| 5,817,120 A | 10/1998 | Rassman | |
| 5,827,297 A | 10/1998 | Boudjema | |
| 5,865,744 A | 2/1999 | Lemelson | |
| 5,895,403 A | 4/1999 | Collinsworth | |

(Continued)

OTHER PUBLICATIONS

Inaba, M. and Inaba, Y., "Androgenetic Alopecia, Modern Concepts of Pathogenesis and Treatment", 29. Operative Treatment for Androgenetic Alopecia, Springer, 1996, pp. 238-244, 309. (9 paQes).

(Continued)

*Primary Examiner* — Ryan Severson
*Assistant Examiner* — Ashley Fishback
(74) *Attorney, Agent, or Firm* — Lena I. Vinitskaya (57) ABSTRACT

Device and method for harvesting and implanting hair follicular units is provided. A combined harvesting and implanting tool or tool assembly provides a harvesting cannula portion detachably coupled to an implanting cannula portion. The harvesting and implanting cannula portions may be coupled by a connector that could be designed to allow for multiple uses of the tool assembly, or alternatively may be designed for single use and rendered non-functional when the implanting cannula portion of the tool is separated from the harvesting cannula portion of the tool.

18 Claims, 5 Drawing Sheets

(56) References Cited

U.S. PATENT DOCUMENTS

| | | |
|---|---|---|
| 6,059,807 A | 5/2000 | Boudjema |
| 6,241,687 B1 | 6/2001 | Voegele et al. |
| 6,306,142 B1 | 10/2001 | Johanson et al. |
| 6,461,369 B1 | 10/2002 | Kim |
| 6,572,625 B1 | 6/2003 | Rassman |
| 6,585,746 B2 | 7/2003 | Gildenberg |
| 7,172,604 B2 | 2/2007 | Cole |
| 7,621,933 B2 | 11/2009 | Bodduluri et al. |
| 7,621,934 B2 | 11/2009 | Bodduluri et al. |
| 2003/0097144 A1 | 5/2003 | Lee |
| 2003/0105414 A1* | 6/2003 | Leong .................. 600/576 |
| 2003/0120298 A1 | 6/2003 | Gildenberg |
| 2004/0092924 A1 | 5/2004 | Vasa |
| 2004/0116942 A1 | 6/2004 | Feller |
| 2004/0193203 A1 | 9/2004 | Pak et al. |
| 2004/0220589 A1 | 11/2004 | Feller |
| 2005/0004592 A1 | 1/2005 | Criscuolo |
| 2005/0096687 A1 | 5/2005 | Rassman et al. |
| 2005/0187573 A1 | 8/2005 | Rassman et al. |
| 2005/0245952 A1 | 11/2005 | Feller |
| 2005/0267506 A1 | 12/2005 | Harris |
| 2006/0161179 A1 | 7/2006 | Kachenmeister |
| 2006/0178678 A1 | 8/2006 | Cole |
| 2006/0293703 A1 | 12/2006 | Pak et al. |
| 2007/0078466 A1 | 4/2007 | Bodduluri et al. |
| 2007/0078475 A1 | 4/2007 | Bodduluri et al. |
| 2010/0030234 A1 | 2/2010 | Bodduluri et al. |

OTHER PUBLICATIONS

Harris, James, A., "New Methodology and Instrumentation for Follicular Unit Extraction: Lower Follicle Transection Rates and Expanded Patient Candidacy," Department of Otolaryngology/Head and Neck Surgery, Univ. of Colorado Health Sciences Center, Denver, Colorado; Copyright 2006 by the American Society of Dermatologic Surgery, Inc. Published by BC Decker, Inc., Dermatologic Surgery, vol. 32, Jan. 1, 2006 (7 pages).

Riordan, Teresa, "Implanting hair is tedious, exacting work—the perfect work for a robot," The New York Times, Monday, Sep. 15, 2003 (1 page).

Non-Final Office Action mailed May 10, 2011, in relation to commonly assigned U.S. Appl. No. 12/577,362 (12 pages).

Response filed Aug. 22, 2011 to Non-Final Office Action dated May 10, 2011, in relation to commonly assigned U.S. Appl. No. 12/577,362 (13 pages).

* cited by examiner

DEVICE AND METHOD FOR HARVESTING AND IMPLANTING FOLLICULAR UNITS

RELATED APPLICATION DATA

This application is a continuation of U.S. patent application Ser. No. 12/049,170, entitled "Device and Method for Harvesting and Implanting Follicular Units," filed Mar. 14, 2008 now U.S. Pat. No. 8,066,717, which claims the benefit under 35 U.S.C. §119 of provisional patent application Ser. No. 60/895,530, filed Mar. 19, 2007.

FIELD OF INVENTION

The present invention relates generally to devices and methods used for harvesting and implanting hair follicular units from and into various areas of the body.

BACKGROUND

Hair transplantation procedures are well-known, and typically involve harvesting donor hair grafts from one area of the body ("donor areas"), and implanting them in another area ("recipient area"). Various procedures and instruments for hair transplantation have been developed and disclosed, including both manual and mechanized processes and instruments to certain degrees of automation. In one well-known process, a linear portion of the scalp is removed from a donor area by dissection, using a scalpel to cut down into the fatty subcutaneous tissue. The strip is then dissected (under a microscope) into the component follicular units, which are then implanted into a recipient area in respective puncture holes made by a needle. Forceps are typically used to grasp and place the follicular unit grafts into the needle puncture locations, although other instruments and methods are known for doing so.

Automated (e.g. robotic) systems and methods for harvesting and implanting hair follicular units have been invented and are currently under commercial development. By way of example, U.S. Pat. No. 6,585,746 to Gildenberg discloses a hair transplantation system utilizing a robotic system, including a robotic arm and a hair follicle introducer associated with the robotic arm.

By way of further examples, U.S. patent application Ser. No. 11/380,903, published as U.S. patent publication 20070078466, and Ser. No 11/421,438, published as U.S. patent publication 20070078475, (both assigned to the assignee of the present application), disclose and describe automated systems for transplanting hair follicular units which employ a multi-part tool assembly carried by a robotic arm. The tool assembly includes an inner, "harvesting" cannula and an outer, "implanting" cannula disposed coaxially over (and moveable relative to) the harvesting cannula. U.S. patent application Ser. Nos. 11/380,903 and 11/421,438 are hereby incorporated by reference for all that they disclose.

SUMMARY OF THE INVENTION

According to one aspect of the present invention, a tool for harvesting and implanting a hair follicular unit is provided. The tool comprises a two part cannula assembly including a harvesting cannula detachably coupled to an implanting cannula, and configured such that a harvested follicular unit carried in the harvesting cannula is movable to the implanting cannula. The harvesting cannula and implanting cannula may be coupled by a connector. Various types of connectors could be used. In one embodiment, the connector may be permanently attached to the harvesting cannula portion of the tool to allow for multiple uses. In the alternative embodiments, the connector may be designed for single use and rendered non-functional when the implanting cannula portion of the tool is separated from the harvesting cannula portion of the tool.

In one exemplary embodiment the connector comprises a sleeve. The sleeve may be coupled, for example, to a proximal end of the harvesting cannula while a distal end of the implanting cannula may be detachably retained within the sleeve, for example, by a frictional interference fit. The connector may be configured to provide for reattachment of a same or different implanting cannula to the harvesting cannula after an initial detachment of the implanting cannula.

In another exemplary embodiment both harvesting and implanting cannula portions may be formed out of a single tubular member and they may be coupled to each other by a perforation in the tubular member at a junction between a proximal end of the harvesting cannula and a distal end of the implanting cannula. The combined harvesting/implanting tool of the present invention may be configured such that detachment of the implanting cannula portion from the harvesting cannula portion renders one or both of the cannulas unfit for reuse, alternatively either one or both cannula portions may be reusable. In some of the embodiments of the present invention, at least one of the harvesting cannula and the implanting cannula may be coupled to a spring actuation device. In further embodiments, the tool assembly of the present invention may be incorporated into substantially automated system, for example, it could be attached to a moveable arm of a robotic system.

According to another aspect of the present invention, a method for harvesting and implanting a hair follicular unit is provided. The method includes harvesting a follicular unit from a body surface, wherein the harvested follicular unit is received into, and carried in, an interior lumen of a harvesting cannula, transferring the harvested hair follicular unit from the interior lumen of the harvesting cannula into an interior lumen of an implanting cannula that is aligned with the harvesting cannula, and implanting the follicular unit from the implanting cannula lumen into a same or different body surface. In one embodiment, the harvesting cannula may be coupled to the implanting cannula at the time of harvesting the follicular unit, and the method further comprises detaching the harvesting cannula from the implanting cannula after the follicular has been transferred from the harvesting cannula lumen into the implanting cannula lumen.

In some embodiments of the method of present invention, the follicular unit may be transferred from the harvesting cannula into the implanting cannula using suction, or a physical displacement member, or both. A separation of the harvesting cannula from the implanting cannula may be performed by a machine that crimps or otherwise crushes or makes non-functional one or both of the harvesting cannula and implanting cannula. Alternatively, the separation of the harvesting cannula from the implanting cannula may be performed in such a manner that one or both of the cannulas are re-usable.

The method may further comprise reattaching the same or a different implanting cannula to the harvesting cannula after the follicular unit has been implanted. In some exemplary embodiments, either one or both of the harvesting and implanting steps of the method of the present invention may be performed substantially automatically, including for example, using robotic assistance.

BRIEF DESCRIPTION OF THE DRAWINGS

Embodiments of the present invention are illustrated by way of example and not limitation in the figures of the accompanying drawings, in which like references indicate similar elements, and in which.

DETAILED DESCRIPTION OF THE ILLUSTRATED EMBODIMENTS

In the following Detailed Description, reference is made to the accompanying drawings that show by way of illustration specific embodiments in which the invention may be practiced. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following Detailed Description, therefore, is not to be taken in a limiting sense.

Figure 1A:
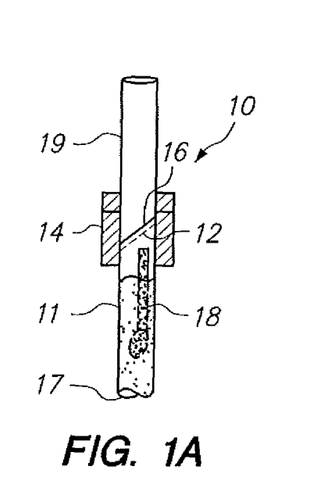
FIGS. 1A-C are partial cut-away side views of one embodiment of a combined (separable) follicular unit harvest-implantation tool assembly of the present invention.
Figures 1B, 1C, 2B:
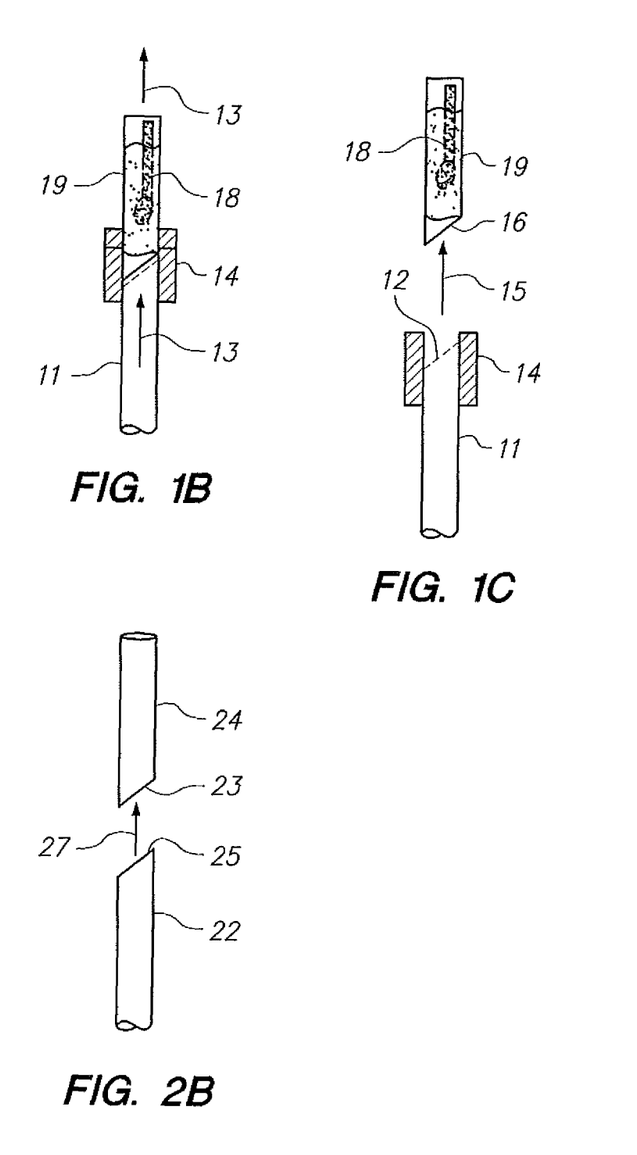
FIGS. 2A-B are side views of another embodiment of a combined (separable) follicular unit harvest-implantation tool assembly of the present invention.

FIGS. 1A-C illustrate a combined harvesting and implanting tool or tool assembly 10 constructed according to one embodiment of the present invention. The term "tool" or "tool assembly" as used herein refers to any number of tools or end effectors that are capable of removing or harvesting tissue, such as hair follicular units, from a body surface or donor area, as well as implanting/inserting substances and objects, such as hair follicular units, into a body surface. In this sense, a body surface can be attached to the body or can be a flap of skin removed from the body. Such tools may have many different forms and configurations. In some embodiments, the tool comprises a hollow tubular shaft. The distal end of removal tools (for example, punches, coring devices, cutting and/or trimming devices, needles), are typically sharpened, to cut and extract the tissue (e.g., hair follicle). Implanting tools may also be sharpened so as to perform a puncture and delivery of the follicular units in one operation. However, the puncture may be formed by another tool, with the implanting tool being relatively blunt and used just for delivery of the follicular units.

The exemplary tool 10 illustrated in FIGS. 1A-C comprises a hollow needle or cannula, and includes a harvesting cannula or harvesting cannula portion 11 having a sloped proximal end 12 that is joined by a breakable connector 14, e.g., comprising plastic or shrink wrap, to a corresponding sloped (or beveled) distal end 16 of an implanting cannula or cannula portion 19. The tool 10 is axially stiff, e.g., made of a hard metal or plastic, and thin-walled to facilitate tissue penetration into the body surface. The implanting cannula portion 19 may have a needle-like tissue piecing (e.g., beveled) distal end 16 used for making incisions at recipient (implantation) sites in a same or different body surface. The harvesting portion 11 may have a tissue-coring (e.g., rough or serrated) distal end 17.

The inner diameters of the respective harvesting and implanting cannulas 11 and 19 may be substantially equal, although the inner diameter of the implanting portion may be slightly larger in some embodiments in order to facilitate transfer of a follicular unit from the harvesting cannula 11 to the implanting cannula (described herein). Similarly, the outer diameters of the respective harvesting and implanting cannulas 11 and 19 may be substantially equal, although it is not essential for practicing the invention. In particular, the respective harvesting and implanting cannula portions 11 and 19 share a common interior lumen so that a hair follicular unit 18 carried in the portion of the lumen within the harvesting cannula 11 may be moved into the portion of the lumen located within the implanting cannula 19 (indicated by arrows 13 in FIG. 1B), e.g., using a suction and/or an obturator, or other physical displacement mechanism (not shown).

The harvesting and implanting portions 11 and 19 preferably share a common interior lumen appropriately sized for harvesting and implanting singular human hair follicular units by first coring the respective follicular units, and then extracting them from a body surface (typically but not necessarily a scalp). By way of non-limiting examples, the interior lumens of the respective harvesting and implanting portions 11 and 19 of tool 10 have a diameter in a range of approximately 0.3 millimeters to 2.0 millimeters. In one embodiment, the shared lumen of both portions is approximately 1 millimeter in diameter. Notably, different sized harvesting and implanting portions 11 and 19 may be used, for example, for harvesting and implanting single-follicle follicular units than are used for harvesting and implanting multi-follicle follicular units.

Once a follicular unit 18 is harvested and transferred from the harvesting portion 11 to the implanting portion 19 of the tool 10, the implanting portion 19 is separated from the harvesting portion 11, as depicted in FIG. 1C, and is ready to be inserted into a recipient location in a same or different body surface or location from where the follicular unit 18 was harvested for implantation of the follicular unit 18. Notably, the size of the puncture hole created by the beveled distal end 16 of the implanting cannula portion 19 may be smaller than it would be if the harvesting cannula portion 11 of the tool 10 was coaxially nested within the implanting cannula portion 19. In addition, by separating the harvesting portion 11 from the implanting portion 19, the beveled distal end 16 of the implanting portion 19 may be kept relatively sharp and sterile until used to facilitate implantation of the follicular 18.

Notably, the harvesting portion 11 of the combined tool 10 may be coupled to the implanting portion 19 using any effective severable-attachment means. In the embodiment of FIGS. 1A-C, the connector 14 may be permanently attached to the harvesting portion 11 to allow for multiple use thereof, e.g., wherein the same or a different implanting portion 19 is reconnected to receive a newly harvested follicular unit 18 from the harvesting portion 11. Alternatively, the connector 14 may be designed for single use and rendered non-functional when the implanting portion 19 is separated from the harvesting portion 11. By way of further example, the separation of the harvesting portion 11 from the implanting portion 19, depicted in FIG. 1C may be performed by a machine that crimps or otherwise crushes the proximal end 12 of the harvesting portion 11, rendering the harvesting portion 11 non-functional (and disposable) after a single use. Alternatively or additionally, the implanting portion 19 may similarly rendered non-functional (and disposed of) after a single use.

Alternatively, the separation of the harvesting portion 11 from the implanting portion 19 may be performed in such a manner that one or both of the harvesting portion 11 and the implanting portion 19 are re-usable. For example, the connector 14 may be a sleeve, wherein the proximal end 12 of the harvesting portion 11 and the distal end 16 of the implanting portion 19 are retained adjacent each other within the sleeve 14 by an interference (frictional) fit. In illustrated example, the harvesting portion 11 is fixed to the sleeve 14, while the implanting portion 19 is removable (as shown in FIG. 1C by arrow 15) by applying enough force to overcome the frictional fit, while maintaining the structural integrity of the respective connector 14 and harvesting portion 11.

Figure 2A:
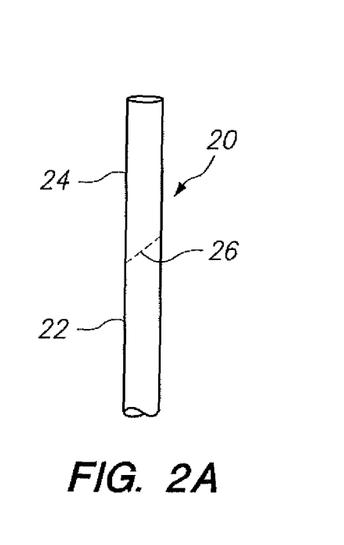

Another embodiment of a combined (separable) harvesting/implanting tool 20 is depicted in FIGS. 2A and 2B. Like tool 10 of FIGS. 1A-1C, tool 20 is a hollow needle or cannula sized and configured for performing the functions of harvesting and implanting hair follicular units from and into a body surface. In particular, tool 20 includes a harvesting portion 22 and an implanting portion 24 that may be separated by breaking apart the tool 20 along a perforation 26. The perforation 26 is preferably made at an angle so that the resulting distal end 23 of the implanting portion 24 has a beveled, tissue piercing shape. Because of the nature of the means of separating the respective harvesting and implanting portions 22 and 24 along the perforation 26, the tool 20 is designed for single use only, since the two portions cannot be reattached for reuse.

As with tool 10, the harvesting and implanting portions 22 and 24 of tool 20 preferably share a common interior lumen appropriately sized for harvesting and implanting hair follicular units by first coring the respective follicular units, and then extracting them from a body surface. By way of non-limiting examples, the interior lumens of the respective harvesting and implanting portions 22 and 24 of tool 20 have a diameter in a range of approximately 0.3 millimeters to 2.0 millimeters. In one embodiment, the shared lumen of both portions is approximately 1 millimeter in diameter. Notably, different sizes of harvesting and implanting portions 22 and 24 may be used. Once a follicular unit (not shown in FIGS. 2A-2B) is harvested and transferred from the harvesting portion 22 to the implanting portion 24 of the tool 20, the implanting portion 22 is separated from the harvesting portion 24, as depicted by the arrow 27 in FIG. 2B, and is ready to be inserted into a recipient location for implantation in a same or different body surface or location from where the follicular unit was harvested.

Figure 3:
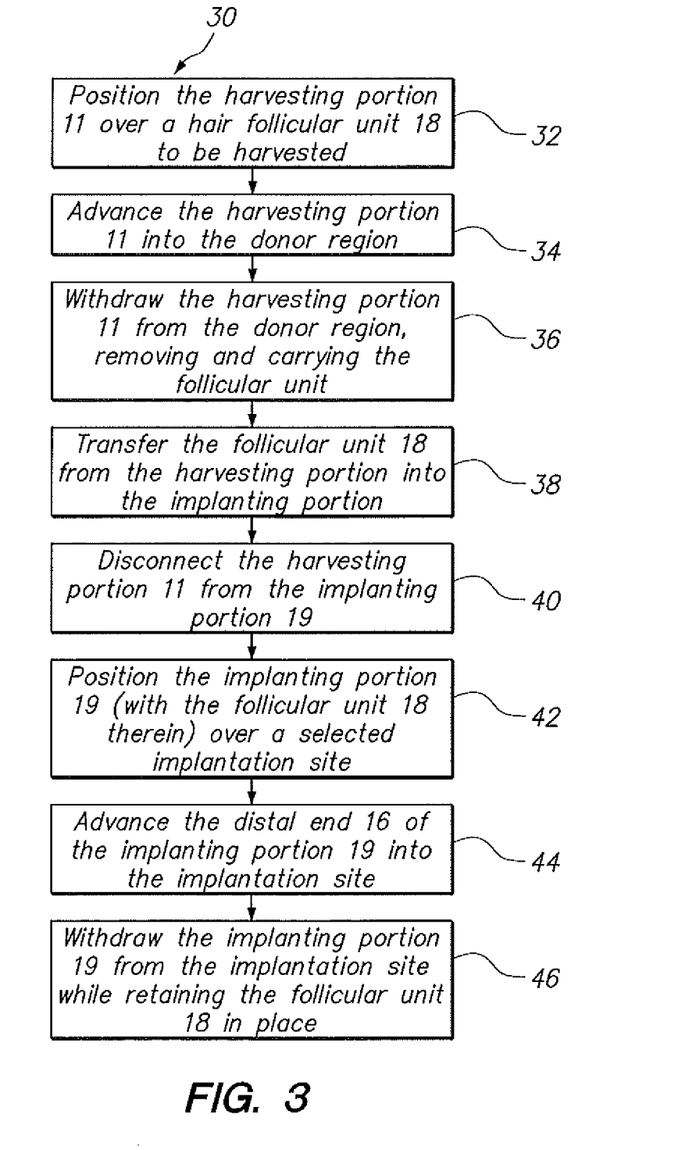
FIG. 3 is a flowchart of a method for harvesting and implanting using a combined follicular unit harvest-implantation tool assembly of the present invention.

FIG. 3 depicts an exemplary method 30 of using the harvesting/implanting tool/tool assembly 10 depicted in FIGS. 1A-1C. It will be appreciated that the method 30 of FIG. 3 may also be performed using the tool 20 depicted in FIGS. 2A-2B. It will also be appreciated that the tools 10 and 20 may be used in both manual (i.e., hand-held) procedures and in procedures employing an automated or semi-automated system, such as robotically-assisted or computer/software/machine-instruction controlled procedures.

The method 30 includes a step 32 of positioning the distal end 17 of the harvesting cannula portion 11 of tool 10 over a hair follicular unit 18 to be harvested from a donor region. At step 34, the harvesting cannula portion 11 is advanced into the donor region, surrounding the follicular unit 18. At step 36, the harvesting cannula portion 11 of the tool 10 is withdrawn from the donor region, removing and carrying the follicular unit 18, which is depicted in FIG. 1A. At step 38, the follicular unit 18 is transferred from the harvesting cannula portion 11 to the implanting cannula portion 19 of the tool 10, so that the most distal (i.e., bottom) end of the follicular unit 18 is positioned just proximally of the beveled distal end 16 of the implanting cannula portion 19, as depicted in FIG. 1B. As noted above, this may be accomplished by selectively connecting a vacuum source to the interior lumen of the tool 10 (i.e., proximally of the implanting portion 19) to draw the follicular unit from the harvesting portion 11 into the implanting portion 19. Alternatively, an obturator or other physical object may be placed through the distal end opening 17 of the tool 10 in order to displace the follicular unit 18 from the harvesting portion 11 into the implanting portion 19. In one embodiment, this is accomplished by lowering the distal end opening 17 of the tool 10 onto a rod sized to fit within the interior lumen of the harvesting portion 11, wherein the rod pushes the follicular unit 18 from the harvesting portion 11 into the implanting portion 19, with or without suction assistance. Further, once inserted into the harvesting portion 11, the rod or other object may be used to break the harvesting portion 11 away from the implanting portion 19 in below step 40, thereby retaining the harvesting portion 11 on the rod or other object.

At step 40, the harvesting portion 11 is disconnected (or otherwise removed) from the implanting portion 19, as depicted in FIG. 1C. In embodiments where the harvesting portion 11 is rendered non-functional after a single use, the method 30 may additionally include a step (not shown) of disposing of the harvesting portion 11 after it is disconnected from the implanting portion 319. At step 42, the implanting portion 19 (with the follicular unit 18 therein) is positioned over a selected implantation site, for example, in the patient's scalp. At step 44, the distal end 16 of the implanting portion 19 is advanced into (thereby puncturing) the implantation site, and the implanting portion 19 is advanced to a desired depth. An obturator is inserted through the lumen of the implanting portion 19 (i.e., in a distal direction from a proximal opening) to retain the follicular unit 18 in place, while (at step 46) the implanting portion 19 is withdrawn from the scalp. At step 18, the obturator is also withdrawn, leaving the newly implanted follicular unit 18 implanted at the implantation site.

As discussed above, one or both of the harvesting and implanting portions 11 and 19 may be alternatively disposable or re-usable. Thus, method 30 may further include steps (not shown) of disposing one or both of the harvesting and implanting portions 11 and 19, or reusing one or both of the harvesting and implanting portions 11 and 19, as the case may be.

In accordance with another aspect of the invention, a combined harvesting and implanting tool assembly may not be initially connected together. Rather, after harvesting a follicular unit, the harvesting cannula may be momentarily aligned with the implanting cannula, and the follicular unit is transferred from the harvesting cannula into the implanting cannula. In particular, with reference to FIG. 4, at step A, the distal end 52 of a harvesting cannula 50 is positioned over a hair follicular unit 54 to be harvested from a donor region 56 of a patient's scalp or other body surface. At step B, the cannula 50 is advanced into the body surface, surrounding the follicular unit 54. At step C, the harvesting cannula 50 is withdrawn from the body surface, removing and carrying the follicular unit 54. At step D, the harvesting cannula 50 is axially aligned with an implanting cannula 60, with the just-harvested follicular unit 54 remaining in the harvesting cannula 50. In particular, the distal end 52 of the harvesting cannula 50 is aligned and, at step E, attached to (or otherwise positioned adjacent) a proximal end 62 of the implanting cannula 60. At step F, for example, an obturator 65 moves the follicular unit 54 from the harvesting cannula 50 into the implanting cannula 60, so that the most distal (i.e., bottom) surface of the follicular unit 54 is positioned just proximally of a beveled distal end 64 of the implanting cannula 60. At step G, the obturator is removed and, at step H, the harvesting cannula 50 is disconnected (or otherwise removed) from the implanting cannula 60. At step I, the implanting cannula 60 (with the follicular unit 54 therein) is positioned over a selected implantation site 66. At step J, the distal end 64 is advanced into (thereby puncturing) the implantation site 66, and the implanting cannula 60 is advanced to a desired depth. An obturator 65' (which may be the same or a different obturator as obturator 65 in step F) is inserted through the lumen of the implanting cannula 60 to retain the follicular unit 54 in place 69, while (at step K) the implanting cannula 60 is withdrawn from the body surface. At step L, the obturator 65' is also withdrawn, leaving the newly implanted follicular unit 54 at the implantation site 66.

Figure 4:
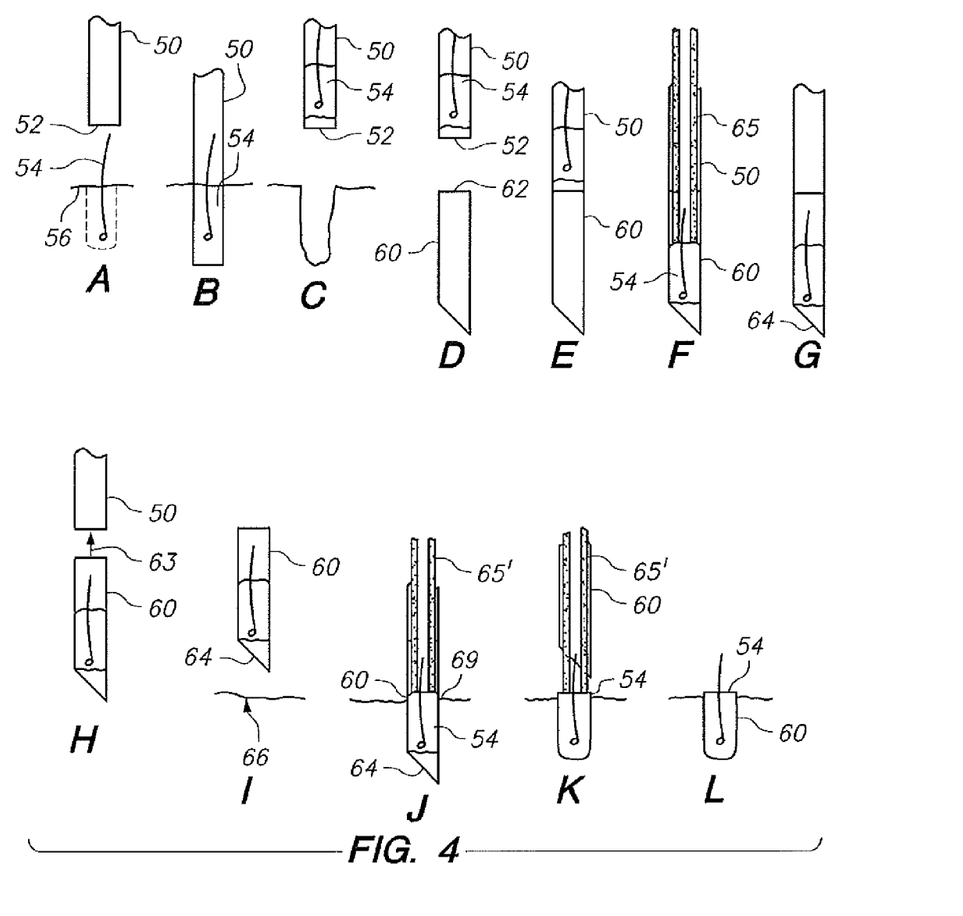
FIG. 4 is a simplified illustration, including partially cut-away views of a harvesting and implantation procedure according to another aspect of the present invention.

The tool assembly (i.e., harvesting cannula 50, implanting cannula 60) used in the method of FIG. 4 may further include an alignment sleeve or holder to facilitate the alignment of the two cannulas for steps D-G. For example, the implanting cannula 60 may be disposed in a holder (not shown) where the proximal surface of the holder extends above the proximal end 62 of the implanting cannula 60 and is configured for receiving the distal end 52 of the harvesting cannula 50 and for aligning the distal end 52 of the harvesting cannula 50 and the proximal end 62 of the implanting cannula 60. Any other effective aligning mechanisms may additionally or alternatively be employed to facilitate the alignment of the harvesting cannula 50 with the implanting cannula 60.

Although some of the examples above were described with reference to harvesting follicular units from one area of the scalp and implanting the harvested units into another area of the scalp, the devices and methods described herein may be used for harvesting follicular units from any area and implanting the harvested units into any area. For example, follicular units may be harvested from and/or implanted into arms, legs, back or other body area skin surfaces. Also, as noted above, the methods of the present invention are useful in manual procedures and systems, as well as in automated or partially automated procedures and systems. Some of the exemplary automated processes described herein are also robotically-assisted or computer/software/machine-instruction controlled.

Figure 5A:
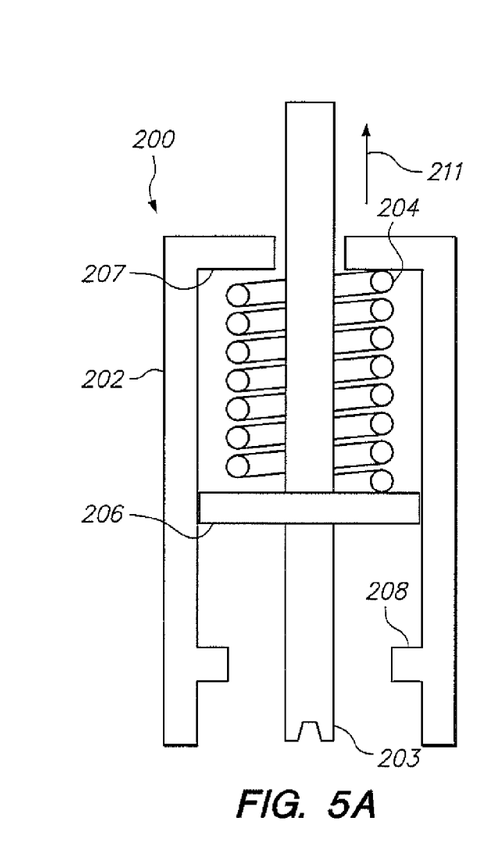
FIGS. 5A-B are cross-sectional side views of a spring-actuation assembly for use in various embodiments of follicular unit harvesting and implantation devices.
Figure 5B:
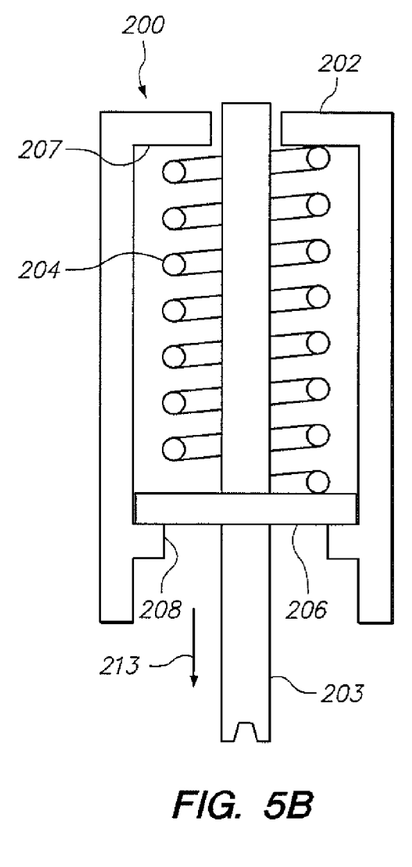

With reference to FIGS. 5A-5B, an embodiment of an assembly 200 for providing spring-force actuation of a harvesting (or implantation) cannula 203 includes a housing 202 and a compression spring 204. The cannula 203 passes through the housing 202 and the center of the compression spring 204. A piston 206 is attached circumferentially to the cannula 203 within the housing 202, with the spring 204 disposed between the piston 206 and a top portion 207 of the housing 202. As such, the spring 204 is compressed when the cannula 202 is retracted through the top portion 207 of the housing 202 (as indicated by arrow 211 in FIG. 5A). The cannula 203 may be held by a conventional means (not shown) with the spring 204 loaded in compression (shown in FIG. 5A). When the cannula 203 released, the stored energy in the spring 204 is also released, and the force of the expanding spring 204 drives the cannula 203 forward as a projectile (indicated by arrow 213 in FIG. 5B), until the piston 206 is stopped by a stop ring 208 in the bottom of the housing 202.

Figure 6:
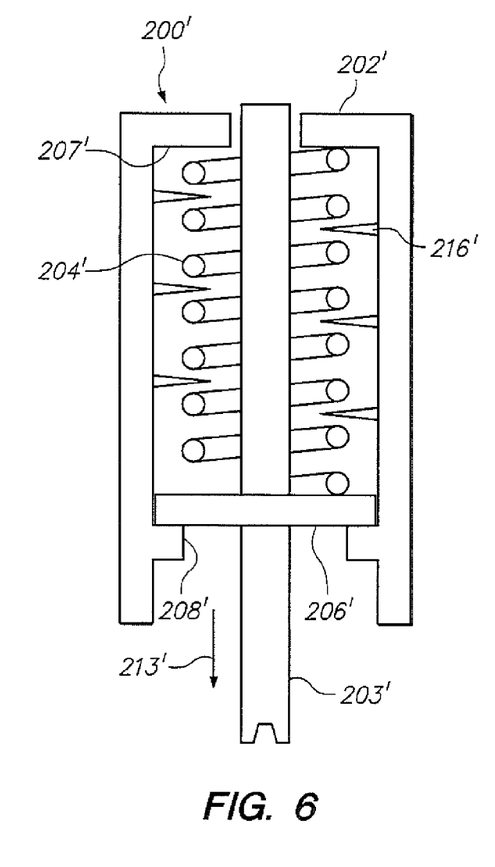
FIG. 6 is a cross-sectional side view of another embodiment of a spring-actuated assembly for use in various embodiments of follicular unit harvesting and implantation devices.

In some embodiments, it is desirable for a harvesting cannula to rotate about its longitudinal axis as it penetrates the body surface to enhance its tissue-coring effectiveness. To facilitate such rotation, the assembly 200' depicted in FIG. 6 is similar to that depicted in FIGS. 5A-5B with the addition of internal threads 216' in the housing 202'. The threads 216' cause the spring 204' to twist during compression and expansion, which in turn causes the cannula 203' to rotate. Such rotation may be useful, especially in conjunction with a harvesting cannula 203' where it is desirable for the cannula 203' to rotate during insertion into the harvesting site.

The depicted and described tool assemblies of the present invention may be hand-held and controlled. In the alternative, the depicted and described tool assemblies may be attached to, and positioned by, a moveable arm of an automated system, e.g., a robotic arm system, as described below with reference to FIGS. 7-8. Movement of one or both of the harvesting and implanting cannulas relative to each other and/or to the remainder of the tool assembly (whether hand-held or carried by an automated positioning system) may be provided by a number of different mechanical, electro-mechanical, pneumatic, hydraulic, magnetic, and other known systems and mechanisms for effecting controlled movement of the respective cannulas.

Movement of the harvesting and implanting cannulas relative to the body surface may be manual, semi-automated, or completely automated. The harvesting and implanting cannulas may be fixed or independently moveable relative to the remainder of the tool assembly, whether the tool assembly is hand-held or attached to a moveable arm. In embodiments in which the tool assembly is carried on an automated (e.g., robotic) arm, movement of the harvesting and implanting cannulas relative to the body surface may be performed by movement of the arm relative to the body surface, movement of the harvesting and implanting cannulas relative to the automated arm, or a combination of each. Similarly, in hand-held embodiments, movement of the harvesting and implanting cannulas relative to the body surface may be performed by movement of the operator's arm relative to the body surface, movement of the harvesting and implanting cannulas relative to the tool assembly, or a combination of each.

In some embodiments, a vacuum source may be selectively placed in communication with the harvesting cannula lumen to apply a proximally directed "pulling" force to facilitate grasping and extracting the follicular units. These features may also be helpful in retaining the follicular unit in the harvesting cannula lumen after it is harvested. In addition, as discussed above, the vacuum source may be used in transferring the follicular unit from the harvesting cannula into the implanting cannula.

Figure 7:
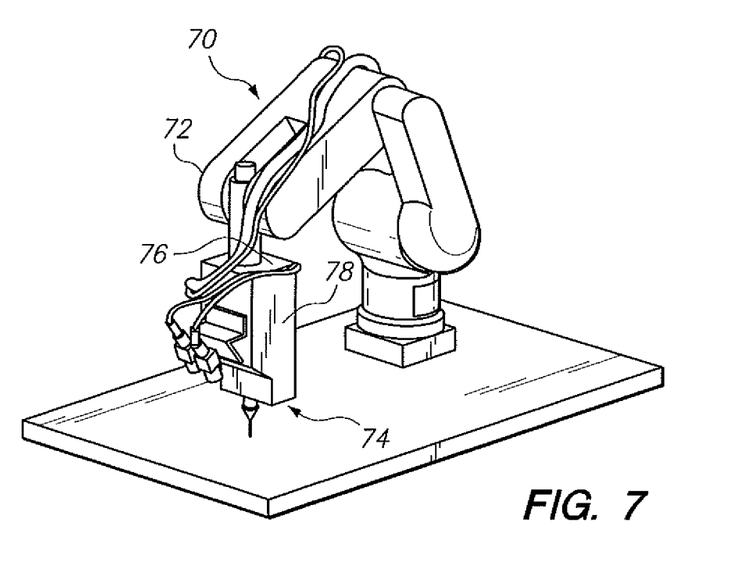
FIGS. 7 and 8 are perspective views of an exemplary robotic system incorporating a combined harvesting-implantation tool assembly of the present invention.
Figure 8:
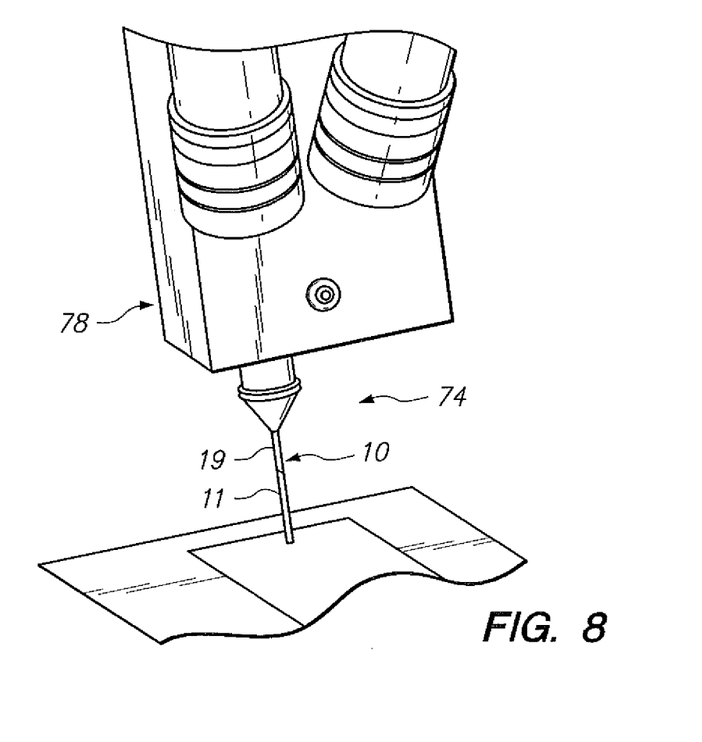

According to another aspect of the present invention, the connectable harvesting/implanting cannulas of the present invention can be used with, and controlled by, automated, semi-automated, or robotic systems. One exemplary embodiment of an image-guided robotic system 70 is shown in FIGS. 7 and 8. The robotic system 70 includes a robotic arm 72 with a maneuverable tool assembly 74 attached to a distal tool plate 76 of the robotic arm 72. In particular, the tool assembly 74 incorporates the combined harvesting/implanting tool 10 depicted in FIGS. 1A-1C, extending from a tool assembly housing 78.

The robotic arm 72 automatically and precisely positions the respective harvesting and implanting cannulas at desired locations, and in desired orientations, along a body surface (e.g., a scalp) of a patient based on control signals derived at least in part from image data acquired by one or more cameras attached to the tool assembly housing 78. Hair transplantation generally includes three steps: follicular unit harvesting, recipient site incision, and follicular unit placement in the incision.

The tool assembly 74 may include a motor drive assembly mounted in the housing 78 and configured to receive and operatively engage the component parts of the tool assembly 74. Above-incorporated U.S. patent application Ser. Nos. 11/380,903 and 11,421,438 disclose an automated (e.g., robotic) system that employs a multi-part tool assembly. A motor drive assembly similar to that described and shown in these applications could be used with the robotic system of the present invention. The motor drive assembly may comprise control circuitry for controlling operation of the respective motors. The control circuitry may include an independent processor associated with the motor drive assembly, which receives as inputs information from the robotic system 70, including but not limited to positioning data obtained from images acquired of the respective cannulas and body surface/objects (e.g., hair follicles). Additionally or alternatively, a respective encoder may be operatively coupled with one or more of the motors for tracking the relative movement and, thus, position information, of the implanting cannula, harvesting cannula, and/or obturator.

In a particular example, the tool 10 depicted in FIGS. 1A-1C is used in the tool assembly 74 of the robotic system depicted in FIGS. 7 and 8. For harvesting a follicular unit from a body surface (e.g., a scalp), the robotic arm 72 positions and aligns the harvesting portion 11 of the tool 10 with a selected follicular unit to be harvested. The harvesting portion 11 is then advanced over the selected follicular unit by motion of the robotic arm 72, accompanied by simultaneous rotational movement of the tool 10 about its longitudinal axis by the motor, with its open distal end 17 penetrating the body surface into the subcutaneous fatty layer underlying the follicular unit in the body surface. In alternate embodiments, a linear drive mechanism may be additionally provided in the motor drive assembly for providing independently controlled axial translation of the tool 10 while it is being rotated. The tool 10 is then withdrawn from the body surface by motion of the robotic arm 72. The harvested follicular unit carried in the lumen of the harvesting portion 11 of the tool 10 is then transferred to the lumen within the implanting portion 19. In some embodiments, a vacuum source may be selectively placed in communication with the harvesting cannula lumen to apply a proximally-directed "pulling" force to facilitate grasping and extracting the follicular unit from the body surface, as well as to help retain the follicular unit in the harvesting cannula lumen after it has been harvested. In addition, as described above, the vacuum source may be used to transfer the follicular unit from the harvesting portion 11 into the implanting portion 19 of the tool 10. Alternatively or additionally, an obturator or pusher member may be used to transfer the follicular unit from the harvesting portion 11 into the implanting portion 19, as described above. The harvesting portion 11 is then disconnected from the implanting portion 19 of the tool, using a manual, automated, or semi-automated procedure.

For implantation, the implanting portion 19 of the tool 10 is repositioned by the robotic arm 72 to a selected implantation site on the body surface, wherein a longitudinal axis of the implanting portion 19 is aligned with a desired intended orientation of the follicular unit 18 when implanted in the body surface. The implanting portion 19 is then advanced into the implantation site by motion of the robotic arm 72, with the sharpened (beveled) distal end 16 of the implanting portion 19 penetrating the body surface to a desired depth. The implanting portion 19 is then withdrawn from the implantation site by motion of the robotic arm 72, with the follicular unit being retained in place at the implantation site by advancing an obturator through the lumen of the tool 10. By way of non-limiting example, the obturator may be advanced by a motor in the housing 78. Thereafter, the obturator may be withdrawn, leaving the newly implanted follicular unit at the implantation site. Alternatively, rather than using the tool 10 of FIGS. 1A-1C, the tool assembly 74 of the robotic system 70 may employ an alternate embodiment of the invention, such as (but not limited to) tool 20 of FIGS. 2A-2B, or the assembly 50/60 of FIG. 4. Thus, the robotic system 70 may similarly be used for harvesting and implanting follicular units using a combined harvesting/implanting tool, as described herein.

The forgoing illustrated and described embodiments of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims. By way of non-limiting example, it will be appreciated by those skilled in the art that the invention is not limited to the use of a robotic system, and that other automated, semi-automated, and manual systems may be used utilizing the connectable cannulas and assemblies of the present invention. By way of another example, it will be appreciated by those skilled in the art that while the foregoing embodiments are described herein in the context of harvesting hair follicular units, the tools and methods are not limited to the harvesting/implanting of hair follicular units, and may be equally used, for example, for removing dermal and sub-dermal tissue that does not contain hair follicular units.

What is claimed is:

1. A tool for harvesting and implanting a hair follicular unit, comprising:
    a two part cannula assembly including 1) a harvesting cannula comprising an open distal end configured to be positioned over and encapsulate a follicular unit and a proximal end, and 2) an implanting cannula comprising a distal end and a proximal end, the implanting cannula configured to implant the follicular unit, the assembly configured to facilitate an unobstructed movement of a harvested follicular unit from a lumen of the harvesting cannula into an unobstructed lumen of the implanting cannula when the proximal end of the harvesting cannula is coupled end-to-end to the distal end of the implanting cannula,
    wherein the harvesting cannula is detachably coupled to the implanting cannula, and upon detachment from the harvesting cannula, the distal end of the implanting cannula has a sharp cutting edge for piercing body tissue.

2. The tool of claim 1, wherein the harvesting cannula is coupled to the implanting cannula by a connector.

3. The tool of claim 2, wherein the connector comprises a sleeve coupled to the proximal end of the harvesting cannula.

4. The tool of claim 3, wherein the distal end of the implanting cannula is detachably retained within the sleeve by a frictional interference fit.

5. The tool of claim 3, wherein the sleeve is configured to provide for reattachment of a same or different implanting cannula to the harvesting cannula after an initial detachment of the implanting cannula.

6. The tool of claim 2, wherein detachment of the implanting cannula from the harvesting cannula renders the connector unfit for reattachment of a same or different implanting cannula to the harvesting cannula.

7. The tool of claim 1, wherein the harvesting cannula and implanting cannula are formed out of a single tubular member.

8. The tool of claim 7, wherein the harvesting cannula is coupled to the implanting cannula by a perforation in the tubular member located at a junction between the proximal end of the harvesting cannula and the distal end of the implanting cannula.

9. The tool of claim 1, configured such that detachment of the implanting cannula from the harvesting cannula renders one or both of the implanting and harvesting cannulas unfit for reuse.

10. The tool of claim 1, wherein at least one of the harvesting cannula and the implanting cannula are coupled to a spring actuation device.

11. The tool of claim 1, wherein the tool is configured such that the harvesting cannula and the implanting cannula move together as a single unit during harvesting of the follicular unit.

12. The tool of claim 1, further comprising a physical displacement mechanism configured to move the harvested follicular unit to the implanting cannula.

13. The tool of claim 12, wherein the physical displacement mechanism comprises a suction mechanism or an obturator.

14. The tool of claim 1, wherein coupling end-to-end comprises aligning the proximal end of the harvesting cannula adjacent the distal end of the implanting cannula.

15. The tool of claim 1, wherein operation of at least one of the harvesting cannula and the implanting cannula is computer controlled.

16. The tool of claim 1, further comprising an alignment mechanism configured to facilitate alignment end-to-end of the harvesting and implanting cannulas.

17. The tool of claim 1, wherein movement of one or both of the harvesting and implanting cannulas is provided by one or more of mechanical, electro-mechanical, pneumatic, hydraulic or magnetic mechanism.

18. The tool of claim 1, wherein the tool is incorporated into a substantially automated system or a robotic system comprising a moveable arm.

* * * * *